United States Patent [19]

Berretti et al.

[11] Patent Number: 4,643,974

[45] Date of Patent: Feb. 17, 1987

[54] DEVICE FOR IDENTIFYING MICROORGANISMS

[75] Inventors: Rodolfo Berretti, Prato; Paolo Tarli, Monteriggioni; Brunilde Berti, San Gimignano, all of Italy

[73] Assignee: Sclavo, S.p.A., Siena, Italy

[21] Appl. No.: 575,334

[22] Filed: Jan. 31, 1984

[30] Foreign Application Priority Data

Feb. 8, 1983 [IT] Italy ............................ 19463 A/83
Jan. 5, 1984 [IT] Italy ............................ 19031 A/84

[51] Int. Cl.⁴ ............................................ C12M 1/00
[52] U.S. Cl. ................................ 435/287; 283/1 A; 434/98; 435/809; 435/299
[58] Field of Search ............. D24/32; 283/900, 1 R, 283/1 A; 434/98; 435/34, 287, 299–301, 809

[56] References Cited

U.S. PATENT DOCUMENTS

| D. 259,141 | 5/1981 | Oliver ........................... D24/32 |
| 807,203 | 12/1905 | Poore ........................... 283/1 A |
| 2,880,865 | 4/1959 | Knox ........................... D24/32 X |
| 3,728,228 | 4/1973 | Duranty ........................ 435/301 |
| 3,891,507 | 6/1975 | Breuer .......................... 435/287 X |
| 3,957,586 | 5/1976 | Babson et al. ................ 435/34 X |
| 4,024,530 | 5/1977 | Hughes ........................ 340/332 |
| 4,056,359 | 11/1977 | Janin ............................ 435/301 |
| 4,258,135 | 3/1981 | Meunier ....................... 435/301 |

Primary Examiner—Samuel Scott
Assistant Examiner—Allen J. Flanigan
Attorney, Agent, or Firm—Hedman, Gibson, Costigan & Hoare

[57] ABSTRACT

A device for determining the presence and identity of a specific microorganism in a biological sample based on biochemical tests is disclosed comprising a set of containers, each of which contains a reagent for performing an individual biochemical test useful for the identification of microorganisms, the set of containers being assembled on a single supporting member which is imprinted with a series of marks adjacent the containers, which marks are indicative of the expected result of a specific microorganism's performance in each biochemical test using the reagent of each individual container, the series of biochemical test containers, reagents and corresponding marks being sufficient to identify a specific microorganism. Series of marks corresponding to the expected biochemical test results for several specific microorganisms are preferably imprinted on the supporting member, making possible the identification of a single microorganism species from among several possibly present. The marks may have different lengths, colors and graphical form or may be also replaced by symbols and/or numbers.

In a preferred embodiment, a device is described for the identification of a single species from among the seven pathogenic species of the Candida genus.

11 Claims, 1 Drawing Figure

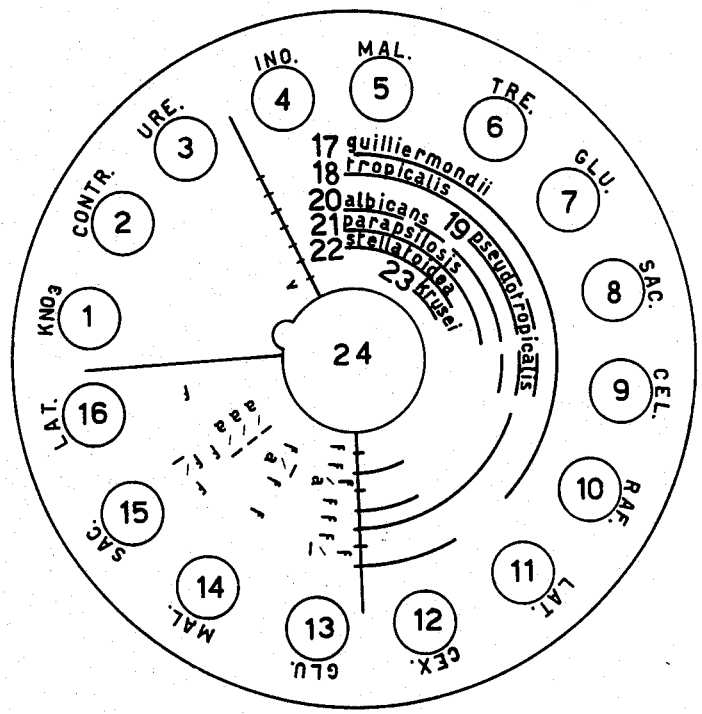

DEVICE FOR IDENTIFYING MICROORGANISMS

This invention relates to a device for identifying microorganisms on the basis of biochemical tests. More particularly, the invention relates to a device for identifying microorganisms which is composed of a set of containers each of, which contain, reagents for the identification of said microorganisms and are assembled on a single supporting member on which there are also imprinted a series of marks correlating the biochemical test results observed in all the containers, in which all the biochemical tests take place, with known biochemical test results for one or more specific microorganisms so as to be sufficient to identify a specific microorganism.

The marks have different lengths, colour and/or graphical form and can also be partially replaced by symbols and/or numbers.

The device is preferably circular in shape and the containers are preferably in the form of test tubes. In order to make the use of the device more convenient, the name of the microorganism to be identified can be written adjacent to its identifying marks on the supporting member.

The reagents for the biochemical tests which are placed in the containers may be in dried, freeze-dried, solid and also compressed in form, or in the form of a solution.

The containers may be an integral part of the device or may be simply inserted into holes provided in the supporting member or adhered to the supporting member. The device may also be provided with a central bore, which is preferably circular.

In order to illustrate the device of the present invention by way of example without limitation, the application of such a device to the identification of the pathogenic species of the Candida genus is described hereinafter.

Many Candida species, and all the pathogenic species among them, are frequently occurring commensals in the natural cavities inside the human body. Such species, under the proper conditions, are capable of causing by endogenous mechanism a number of diseases.

In addition to *Candida albicans,* which is the most frequently isolated species, at least six different Candida species, viz.: *Candida stellatoidea, Candida krusei, Candida tropicalis, Candida pseudotropicalis, Candida quillermondii, Candida parapsilosis* are also regarded as pathogenic.

Therefore, from a diagnostic standpoint, once a *Candida culture has been isolated, it is necessary to determine whether a species which is pathogenic in humans is present.*

Identification of the species to which the microorganism concerned belongs is made by resorting to biochemical tests, such as:

(a) Assimilation of various sugars in a culturing medium which is devoid of any other carbon sources (C-auxanorgram);

(b) Fermentation tests for various sugars, and (c) Growth in the presence of certain substances.

The assimilation tests are performed by preparing a germ-agar, with the slurry of the strain to be identified and the specific C-auxanogram medium. On the germ-agar there are deposited either paper discs which have been soaked at the very moment of use with different sugar solutions, or paper discs carrying the sugars concerned in dry form. Alternatively, porcelain well which contain the sugar solutions may also be used.

It is possible to use specialized plates, which have a sector partition on their lower surfaces.

If such a specialized plate is used, separate containers for testing assimilation of different sugars are already present, and the practitioner need only label the individual containers or wells to indicate the sugar container in each.

The results of the assimilation tests are read after an incubation at 25° C.-37° C. for 24 to 48 hours. As growth halos are observed around the assimilation sugars, these halos are regarded as positive test results and indicated by symbols (+). The absence of growth is indicated with a contrasting symbol (−).

Fermentation tests are usually carried out after having performed the auxanogram, because they complete the latter test: as a matter of fact a sugar which has not been assimilated cannot be fermented. Only the assimilated sugars are thus tested.

The tests can be prepared in yeast water or in solutions which contain vitamin factors at a preselected concenration and with an appropriate concentration of the sugar to be tested. In order to evidence gas evolution Durham bubble caps can be used, or an admixture of paraffin wax and petroleum jelly.

The performance of these tests requires the inoculation of the slurry to be tested, its incubation at 25° C.-37° C. and daily readouts for up to 10 days of incubation.

Subsequently, it is possible to relate the test results to those reported for particular the species by referring to specially prepared tables as reported in many reference books, among which the following can be mentioned: J. Lodder, 1970 Edn., The Yeast, North Holland Publishing Co., Amsterdam.

Carbohydrate assimilation and fermentation tests can be carried out with commercially available kits ready for use. Among these, the "API 20 C Yeast System (Analytab Products, Inc., New York) and the "Uni-Yeast Tek System" (Flow Diagnostics) can be mentioned.

API 20 C consists of a 20-cell tunnel, the cells containing dehydrated carbohydrates for the assimilation and fermentation tests.

The cells are filled with a slurry of the fungus to be tested, as prepared in an agar furnished with the kit which is dissolved and cooled to 50° C. After an incubation at 30° C. for 48 to 72 hours, the fermentation of the sugars is indicated by the colour change of an indicator and the production of gas, which is indicated by the formation of bubbles.

The assimilation of the carbohydrates is indicated by the growth of the strain in the cells.

The Uni-Yeast Tek System consists of two test tubes and a multipartitioned Petri dish. The tests tubes contain culturing media for the detection of germinative pseudotubules and assimilation of sucrose, respectively, and it possible to identify *C. Stellatoridea.* The dish has 11 peripheral compartments which contain solid media for the fermentation of carbohydrates, for the detection of urease and for the assimilation of carbohydrates and nitrates. At the centre of the dish there is a small cell which contains corn meal agar for detecting mycelium and chlamidopspores.

The dish is inoculated with a drop of a slurry in distilled water of the fungus being tested and is incubated at 25° C. from 2 to 7 days.

The device of the present invention makes it possible to identify a particular species of microorganism contained in a biological sample. In a preferred embodiment, a specific pathogenic species of microorganism belonging to the Candida genus is identified, in a simple and efficient way using assimilation and fermentation tests of a few sugars, testing for growth in the presence of $KNO_3$ and in the presence of cycloheximide, and for the ability to produce urease.

The device in question, preferably having a circular shape, has on its top surface a set of containers, which are preferably in the form of test tubes or a set of hollow spaces. The number of containers or spaces is at least 16 for the particular embodiment which relates to the Candida genus.

The containers hold the reagents for the biochemical tests, in any of the forms mentioned hereinabove.

On the top surface, there are marks of different lengths, colour and/or graphical form (also partially replaced by symbols and/or figures) adjacent to the containers, a series of marks for each of the Candida species to be considered and which indicate the performance in each biological test that is characteristic of the individual Candida species, which series of marks together are sufficient to identify a specific microorganism from among the possible species considered. Along the mark it is possible to inscribe the name of the Candida species to be identified.

Such a device provides a unified laboratory apparatus for testing a microorganism sample for the sugars assimilated and fermented, while simultaneously ascertaining growth with $KNO_3$ being present, cycloheximide sensitivity, and the capacity of producing urease.

It is thus rapidly and efficiently possible to relate the performance of a sample in a series of biological tests to the species to be identified.

FIG. 1 shows a possible embodiment of the device for identifying the pathogenic species of Candida.

In the device, there are seven arc-of-circle marks 17-23 having different lengths. The seven marks (17-23) are preferably of different colours to further differentiate the marks, however the colour type is not critical and in the list reported hereunder, the colours are indicated, by way of illustration, to correspond to the several identifiable species:

Yellow: *Candida guillermondii* (17)
Red: *Candida albicans* (20)
Green: *Candida parapsilosis* (21)
White: *Candida pseudotropicalis* (19)
Sky-blue: *Candida tropicalis* (18)
Violet: *Candida krusei* (23)
Orange: *Candida stellatoidea* (22)

In addition, if the mark adjacent a particular test container is continuous (—) the characteristic test result for the species corresponding to the marks is positive, whereas, if the mark is discontinuous (- - - -) the characteristic test result for that species is variable and, lastly, if the mark is lacking the test result characteristic of that species is negative.

The device also reports symbols which have the following meanings:
f: for fermentation
a: for acidifying
f/a: for fermentation or acidifying
—/a: for negative or acidifying
f/—: for fermentation or negative
v: for variable A sugar is fermented if there is production of acid and carbon dioxide.

A sugar is acidified if there is only a production of acid.

At the centre of the device there is a central bore 24, which, at the instant at which the Petri dish is positioned, serves to deposit a certain volume of water so as to moisten the environment. The reagents for the biochemical tests are placed in the 16 containers from 1 to 16 inclusive in any of the forms which have already been described and can be identified after the symbols of the reagents.

The 16 containers hold the following regents:
Fermentation tests:
Glucose (GLU) (13)
Maltose (MAL) (14)
Sucrose (SAC) (15)
Lactose (LAT) (16)
Growth tests:
$KNO_3$ (1)
Cycloheximide+glucose (CEX) (12)
Urease production:
Urea (URE) (3)
Assimilation tests
Inositol (INO) (4)
Maltose (MAL) (5)
Trehalose (TRE) (6)
Glucose (GLU) (7)
Sucrose (SAC) (8)
Cellobiose (CEL) (9)
Raffinose (RAF) (10)
Lactose (LAT) (11)
Control tests:
no reagent (2)
(for the nitrogen assimilation test)

pH indicators can be added to the reagents in order to make the reactions more conspicuous.

For the identification of the pathogenic species of the Candida genus, the procedure scheme is as follows: the device of FIG. 1 is placed in a Petri dish and the eight containers which contain the sugars to be tested in the assimilation tests, as listed hereinabove, and the container which holds the cycloheximide are filled with a solidifiable culturing medium having no further carbon sources, with or without a pH indicator. The container for the nitrogen source assimilation test and the control container (comparison) are filled with another solidifiable culturing medium, with or without a pH indicator and devoid of any nitrogen sources.

The slurry of the microorganism sample to be tested is then prepared, by taking it from an isolation plate (eg Sabourand) and with it there are inoculated all the containers for the fermentation tests as enumerated above, the urea-containing container is inoculated, and, in addition, a drop of the slurry is deposited in the containers with the already solidified culturing media.

The containers intended for the fermentation tests are then closed with previously melted petroleum jelly. The entire assembly is then incubated at 25° C.–30° C.

On completion of the incubation stage, the sugar assimilation tests are evaluated: if the tested sample the expected microorganism is present, there will be growth or colour change in the pH indicator, otherwise no change shall be observed.

The colour is observed of the mark which unites the assimilation test to the cyclohexemide growth test which have given positive results (growth or colour change of the pH indicator) and the species of the Candida genus is determined.

For example, if the assimilation tests in maltose (MAL), trehalose (TRE), glucose (GLU) and that of growth in cyclohexemide prove positive, this means that Candida stellatoidea (continuous orange line) is present. By following the coloured mark along its circumference, one reads the results of the biochemical tests which confirm the identification: in the case of Candida stellatoidea, the fermentation tests for glucose (GLU), and maltose (MAL) will be positive (f) whereas that of sucrose (SAC) will be negative (−/a).

The control test serves as a reference for the nitrogen source assimilation test ($KNO_3$).

The device, the subject of the present application, for example the one shown in FIG. 1, can serve also for the identification of other pathogenic yeasts: their identification is based on similar tests made with the same procedure and takes place with the help of a table in which the results of such tests have been inscribed.

Such tables are reported in many specific reference books, such as J. Lodder, 1970 Edn., The Yeast, North Holland Publishing Co., Amsterdam.

EXAMPLE

In the device shown in FIG. 1 the reagents for the sugar assimilation tests are represented by solutions of the several sugars (20% to 40%) in distilled water, with polyvinyl alcohol (1% to 0.5%). The reagent for the potassium nitrate assimilation test is a solution of $KNO_3$ at the concentration of 10% in 1% to 0.5% polyvinyl alcohol.

No reagents are present in the control solution for nitrogen assimilation.

The reagent for the cycloheximide sensitivity test is a solution of glucose of 20% concentration in distilled water and polyvinyl alcohol (1% to 0.5%) and cycloheximide (0.5%).

For the urease production test the reagent is a specific Christensen type broth with a pH indicator.

The reagents for the fermentation tests are a conventional specific broth based on oxmeat extract, sodium chloride, and distilled water, which separately contains the individual sugars at the concentration of 2% and bromothymol blue is the pH indicator. Portions of 100 microliters of each solution are deposited in the respective containers.

At this stage, the device is placed in an apparatus wherein the reagents undergo a drying cycle, for example under a vacuum.

On completion of such a cycle, the device such be placed into an envelope of an appropriate material, such as a plastics material (alone or within a Petri dish), which is sealed.

Sterilization can be carried out either with ethylene oxide or with gamma rays. After such a procedure, the device (alone or within a Petri dish) is slipped into an envelope of a material which gives sufficient safety against moisture effects.

The devices so prepared can be stored also for a long time at $+2°$ C.$-+8°$ C. prior to being used for identifying the microorganisms.

The culturing medium for the sugar assimilation test is based on Y.B.N. (Difco), 2% agar-agar, and bromocresol purple as the pH indicator.

The culturing medium for the nitrogen source assimilation test is based on Y.C.B. (Difco), 2% agar-agar and bromothymol blue as the pH indicator.

We claim:

1. A device for the identification of microorganisms based on biomedical tests and consisting of a plurality of containers assembled on a single supporting member, each container holding the reagents necessary to perform an individual biochemical test on a microorganism-containing sample introduced therein, said supporting member exhibiting on its surface one or more series of marks adjacent the containers corresponding to a particular microorganism and indicating, for each biochemical test for which reagents are held in the adjacent containers, the characteristic performance of said particular microorganism in each of said tests, which series of marks is sufficient for identifying a specific microorganism.

2. Device according to claim 1, wherein the reagents are in the form of dried or freeze fried solutions, or are solids or in tablet form.

3. Device according to claim 1, wherein the marks have different lengths, colours and/or graphical form and can also be partially replaced by symbols and/or figures.

4. Device according to claim 1, wherein such containers are an integral part of the supporting member or are fixed on the top surface thereof by adhesion of insertion therein.

5. Device according to claim 1, wherein a central bore can be formed therethrough.

6. Device according to claim 1, wherein the microorganism is a yeast.

7. Device according to claim 1, wherein the microorganism belongs to a pathogenic species of the Candida genus.

8. Device according to claim 1, wherein the microorganism is a member of the group, Candida albicans, Candida stellatoidea, Candida krusei, Candida tropicalis, Candida guillermondii, Candida parapsilosis, and Candida pseudotropicalis.

9. Device according to any one of claims 7 and 8, wherein the containers in the device are 16 in number.

10. Device according to any one of claims 7 and 8, wherein the reagents include $KNO_3$, cycloheximide plus glucose, urea, glucose alone, sucrose, lactose, maltose, raffinose, cellobiose, inositol, trehalose.

11. A method for the identification of a particular microorganism contained in a biological sample conprising adding an amount of said biological sample or a slurry thereof to each of the containers of the device according to claim 1 sufficient to perform said biochemical tests.

* * * * *